US00PP18476P2

(12) United States Plant Patent
Irie

(10) Patent No.: US PP18,476 P2
(45) Date of Patent: Feb. 5, 2008

(54) *HYDRANGEA* PLANT NAMED 'RIE13'

(50) Latin Name: *Hydrangea macrophylla*
Varietal Denomination: RIE 13

(76) Inventor: Ryoji Irie, 3-7 Narutaki Honmachi Ukyoku, Kyoto (JP)

( * ) Notice: Subject to any disclaimer, the term of this patent is extended or adjusted under 35 U.S.C. 154(b) by 0 days.

(21) Appl. No.: 11/525,496

(22) Filed: Sep. 22, 2006

(51) Int. Cl.
*A01H 5/00* (2006.01)

(52) U.S. Cl. ..... Plt./250

(58) Field of Classification Search ..... Plt./250
See application file for complete search history.

(56) References Cited

U.S. PATENT DOCUMENTS

PP16,613 P2 * 6/2006 Irie ..... Plt./250

* cited by examiner

*Primary Examiner*—Wendy Haas

(57) ABSTRACT

A new cultivar of *Hydrangea* plant named 'RIE 13' that is characterized by broad upright habit, large dark grey-green leaves and fertile flowers which carry bi-colored pink and light purple bracts. In combination these traits set 'RIE 13' apart from all other existing varieties of *Hydrangea* known to the inventor.

3 Drawing Sheets

Genus: *Hydrangea. Species: marcophylla.*
Denomination: 'RIE 13'.

BACKGROUND OF THE INVENTION

The present invention relates to a new and distinct cultivar of *hydrangea* that is grown for use as an indoor floral potted plant and an outdoor ornamental flowering shrub. The new cultivar is known botanically as *Hydrangea macrophylla* and will be referred to hereinafter by the cultivar name 'RIE 13'.

'RIE 13' resulted from a breeding program that was conducted by the inventor at the inventor's nursery in Kyoto, Japan and began in 1990. The purpose of the breeding program was to produce new varieties of floral potted *hydrangeas* that exhibit new and unique flowers and flower color.

Between May 1990 and May 1993 the inventor assembled a collection of unnamed and unreleased hybrids from a sequence of deliberate pollinations involving the following cultivars, all unpatented, and available in commerce in Japan: *Hydrangea macrophylla* 'Otafuku', *Hydrangea macrophylla,* 'Yamaajisai', and *Hydrangea macrophylla* 'Fijinishiritaki'. The inventor did not record which variety was used as male parent and which as female parent. In May 1993, the inventor carried out a deliberate pollination between one unnamed plant from the inventor's collection as female parent and the variety *Hydrangea macrophylla* 'Sumidanohanabi' (unpatented) as male parent.

The pollination described above produced thirty-five individual varieties, which the inventor considered novel and unusual. One of these individual varieties was selected by the inventor in June 1994 and is the subject of the present invention, 'RIE 13'.

'RIE 13' is a deciduous shrub that exhibits large dark grey-green leaves and individual fertile flowers which carry bi-colored pink and light purple bracts. 'RIE 13' is distinguishable from the parent plants by flower color, and unique inflorescence development, which produces an average of 600 fertile flowers per inflorescence. Of these 600 flowers, some 450 flowers carry the bi-colored bracts. No sterile flowers are present. The closest cultivar of *hydrangea* known to the inventor is the inventor's variety *Hydrangea* 'RIE 09' (U.S. Plant Pat. No. 16,613). Whereas 'RIE 13' bears only fertile flowers, many with colored bracts, 'RIE 09' bears both sterile flowers and fertile flowers whose bracts are uniformly pink.

'RIE 13' was first asexually propagated by the inventor, in the spring of 1995 in a cultivated area of Kyoto, Japan. The method used for asexual propagation was softwood cuttings. The characteristics of the new *Hydrangea* cultivar named 'RIE 13' have been determined stable and are reproduced true to type in successive generations.

SUMMARY OF THE INVENTION

The following traits have repeatedly observed and represent the characteristics of the new *Hydrangea* cultivar 'RIE 13'. These traits in combination distinguish 'RIE 13' from all other commercial varieties of *Hydrangea* known to the inventor. 'RIE 13' has not been tested under all possible conditions and phenotypic differences may be observed with variations in environmental, climatic and cultural conditions, without however, any difference in genotype.

1. *Hydrangea* 'RIE 13' is grown for use as both an indoor floral potted plant and an outdoor ornamental flowering shrub.
2. *Hydrangea* 'RIE 13' exhibits individual fertile flowers many of which carry bi-colored pink and light purple bracts.
3. *Hydrangea* 'RIE 13' exhibits unique inflorescence development that produces an average of 600 fertile flowers and no sterile flowers per inflorescence.
4. *Hydrangea* 'RIE 13' exhibits a broad upright habit.
5. *Hydrangea* 'RIE 13' exhibits large dark grey-green leaves.
6. *Hydrangea* 'RIE 13' is 24.5 cm in height and 35 cm in diameter in a 1.5-liter container.

7. *Hydrangea* 'RIE 13' is a deciduous shrub.
8. *Hydrangea* 'RIE 13' exhibits rigid, strong basal branches.
9. *Hydrangea* 'RIE 13' is hardy to USDA Zone 5.
10. *Hydrangea* 'RIE 13' blooms continuously from early April to October.

BRIEF DESCRIPTION OF THE DRAWINGS

The accompanying color drawings illustrate the overall appearance of the new *Hydrangea* cultivar 'RIE 13' showing the colors as true as it is reasonably possible to obtain in colored reproductions of this type. Colors in the photographs may differ from the color values cited in the detailed botanical description, which accurately describe the actual colors of the new variety of *Hydrangea* named 'RIE 13'. Photographs are of plants grown in a frost-protected greenhouse in De Kwakel, The Netherlands. The plants are approximately twenty one months old. The plants were produced from a cutting which was rooted and grown in a four inch container, then transplanted into the 1.5 liter container, then pinched to encourage basal branching, then allowed to shoot from the base and allowed to flower in its natural season.

The drawing labeled as FIG. 1 depicts an individual whole plant growing in a 1.5-liter container.

Figure 1:
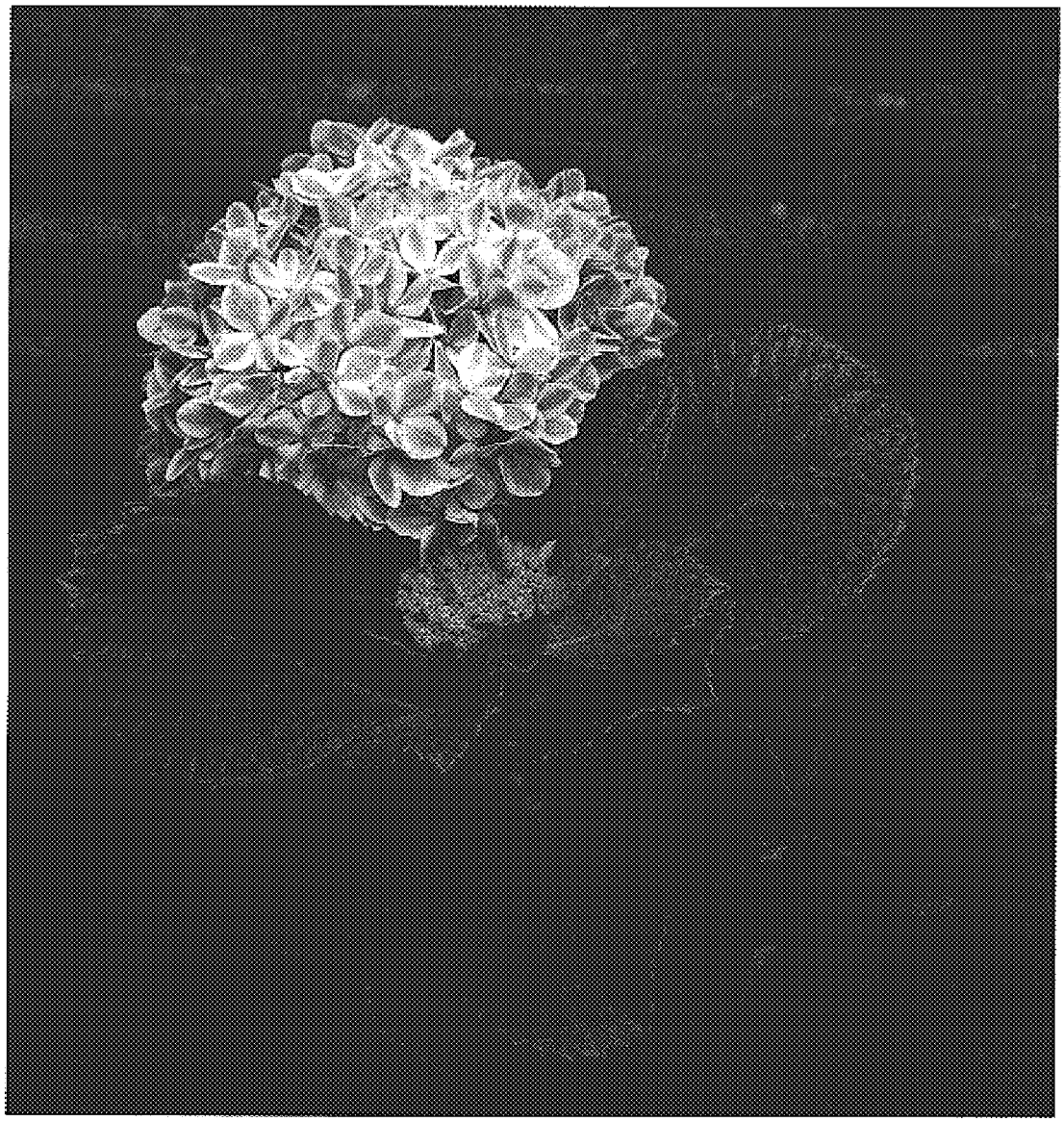
Figure 2:
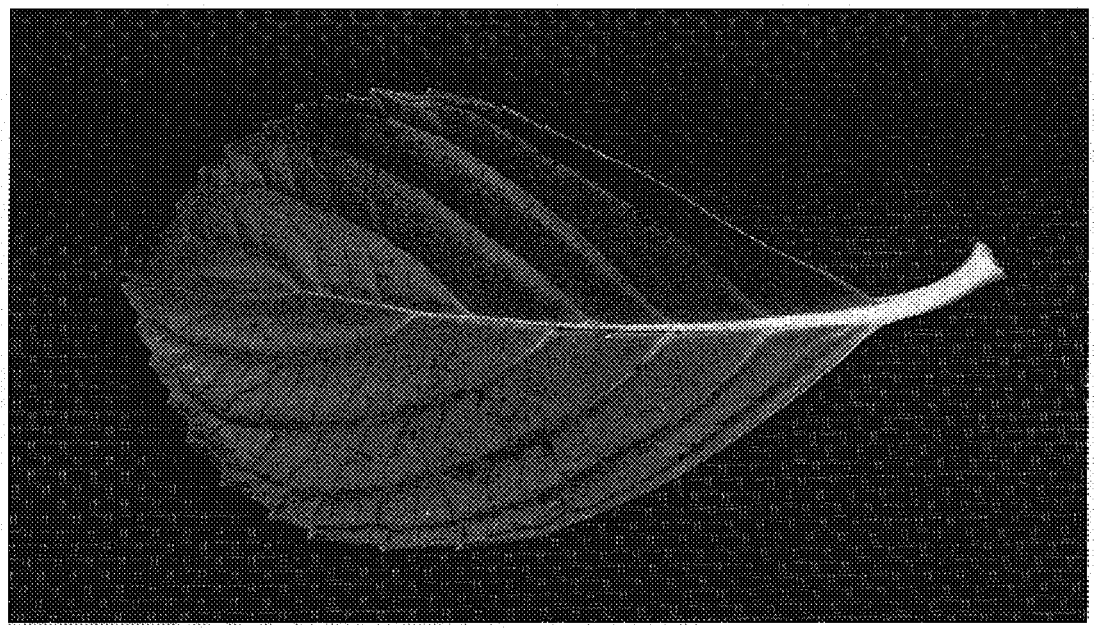

The drawing labeled as FIG. 2 illustrates a leaf of 'RIE 13'.

Figure 3:
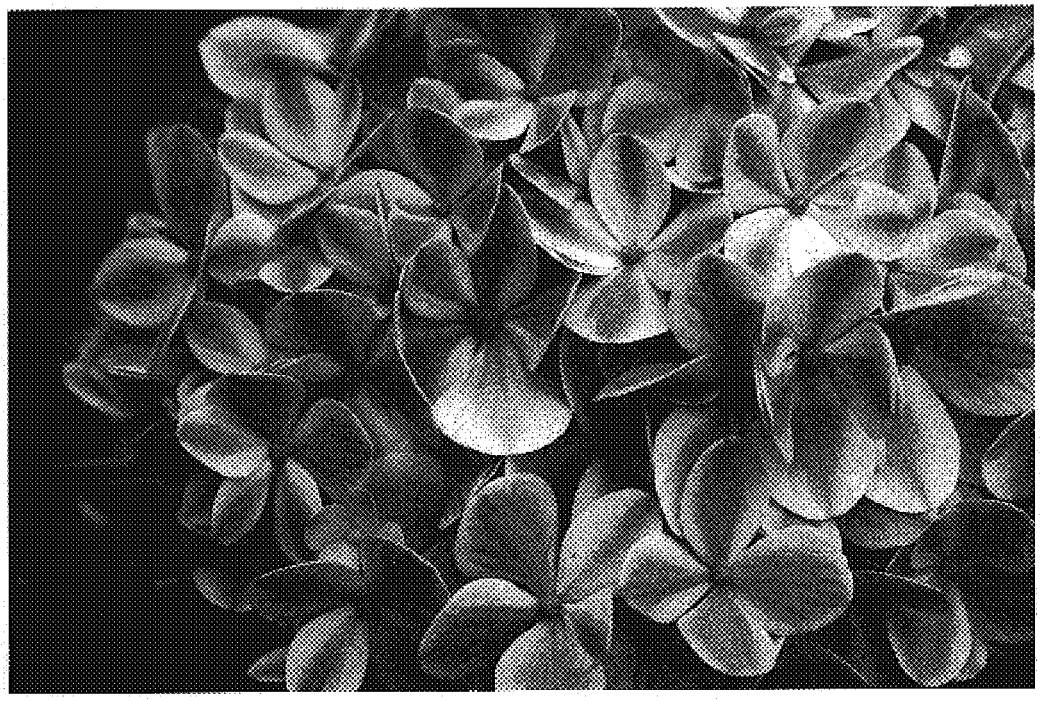

The drawing labeled FIG. 3 illustrates the inflorescence of 'RIE 13'.

All drawings were made using conventional techniques and although colors may appear different from actual colors due to light reflectance they are as accurate as possible, by conventional photography.

BOTANICAL DESCRIPTION OF THE PLANT

The following is the detailed description of 'RIE 13' as grown in a greenhouse in De Kwakel, The Netherlands. Data was collected in April 2004 from 12-month-old plants grown in 1.5-liter containers. The color determinations are in accordance with the 2001 Edition of the Colour Chart of The Royal Horticultural Society, London, England, except where general color terms of ordinary dictionary significance are used. The growing requirements are similar to the species.

Botanical classification: *Hydrangea macrophylla* 'RIE 13'.
Genus: *Hydrangea.*
Species: *macrophylla.*
Denomination: 'RIE 13'.
Commercial classification: Floral plant, ornamental shrub.
Common name: *Hydrangea.*
Use: Grown for use as a potted indoor plant or as an outdoor ornamental flowering shrub.
Container size: Suggested container size is 1.5-liter.
Cultural requirements: Performs best when planted in loam based moisture retentive soil, in partial shade, with regular water.
Parentage: *Hydrangea macrophylla* 'RIE 13' is a hybrid plant that resulted from the induced cross-pollination of the following parent plants:
- *Female parent.*—An unnamed individual *Hydrangea macrophylla.*
- *Male parent.*—An individual *Hydrangea macrophylla* 'Sumidanohanabi' (unpatented).

Plant description:
- *Blooming seasons.*—Spring and summer (natural season) or year-round if forced.
- *Plant habit.*—Broad upright.
- *Plant type.*—Deciduous shrub.
- *Overall plant shape.*—Broad inverted triangle.
- *Vigor.*—Moderate to low.
- *Growth rate.*—An average of 8 cm per month in spring.
- *Plant height.*—24.5 cm in height.
- *Plant diameter.*—35 cm in diameter.
- *Hardiness.*—USDA Zone 5.
- *High temperature tolerance.*—Tolerant to 32° Centigrade.
- *Root system.*—Fibrous.
- *Propagation.*—Propagation is accomplished by the method of softwood cuttings.
- *Time and temperatures to develop roots.*—Approximately 4 weeks is needed to develop roots on an initial cutting, at temperatures of 18° to 20° Centigrade.
- *Crop time* (*outdoor plant crop*).—An average of 12 months is needed to produce a commercial container size flowering outdoor plant, from a rooted cutting.
- *Temperatures* (*outdoor plant crop*).—From rooted cuttings to commercial size containers, the outdoor crop is grown at natural outdoor temperatures utilizing unheated greenhouses for winter protection.
- *Crop time* (*indoor plant crop*).—An average of 4–6 months is needed to produce a commercial container size flowering indoor plant, from a rooted cutting.
- *Temperatures* (*indoor plant crop*).—Transplant rooted cuttings to liner pots and keep for a minimum of 6 weeks at below 5° Centigrade to force dormancy. Transplant to 1.5-liter containers and keep at 18° to 25° Centigrade for a minimum or 10 weeks to produce commercial container size flowering plants.
- *Disease and pest resistance or susceptibility.*—No susceptibility to pests or disease known to the inventor.

Stem:
- *Number of lateral branches.*—An average of 4 lateral branches.
- *Lateral branch length.*—Average is 14.6 cm in length.
- *Lateral branch diameter.*—Average is 6 mm in diameter.
- *Stem shape.*—Rounded.
- *Stem surface.*—Moderately glossy.
- *Pubescence.*—None observed.
- *Stem strength.*—Strong.
- *Stem texture.*—Rigid.
- *Stem color.*—144A and 144B.
- *Lenticels.*—Present.
- *Quantity of lenticels.*—An average of 5 per cubic cm of stem surface.
- *Lenticel color.*—A combination of colors N186B and N186C is present on an individual lenticel.
- *Lenticel dimensions.*—An average of 1.5 mm in length and 0.5 mm in width.
- *Lenticel color.*—183A.
- *Branching habit.*—Moderately branching.
- *Branching requirements.*—Pinching encourages lateral branching.
- *Internode length.*—1.9 cm between nodes.

Foliage:
- *Type.*—Deciduous.
- *Arrangement.*—Opposite.
- *Division.*—Simple.

*Quantity of leaves per lateral stem.*—An average of 16 individual leaves per lateral stem.

*Leaf.*—Shape: Obovate. Apex: Acute. Base: Attenuate. Margins: Serrate. Dimensions: An average of 14.3 cm in length and 9.1 cm in width. Texture: Smooth, moderately glossy. Pubescence: None present. Venation pattern: Pinnate. Vein color (adaxial surfaces): 145B. Vein color (adaxial surfaces): 145C. Young leaf color (adaxial surfaces): 143A and 143B. Young leaf color (abaxial surfaces): 143B. Mature leaf color (adaxial surfaces): 139A. Mature leaf color (abaxial surfaces): 145C.

*Attachment.*—Petiolate.

*Petiole dimensions.*—An average of 2.1 cm in length and 4 mm in width.

*Petiole color.*—Between 144C and 145B.

*Durability of foliage to stress.*—High durability to stress.

*Stipules, tendrils, thorns.*—None observed.

*Fragrance.*—None observed.

Flowers:

*Flower arrangement.*—Terminal globular compound corymb.

*Inflorescence type.*—Compound corymb.

*Inflorescence dimensions.*—An average of 15.6 cm in height and 21.9 cm in width.

*Flowering habit.*—Continuously from early April to October.

*Quantity of flowers.*—Approximately 600, all fertile, of which approximately 450 flowers have bracts and approximately 150 flowers are without bracts.

*Flower type.*—Rotate.

*Bud.*—Dimensions: An average of 4 mm in length and 2.5 mm in width. Shape: Ovate. Color: 144b.

*Flower aspect.*—All directions.

*Rate of opening.*—Flowers open approximately 5 days after buds form.

*Flowers.*—Dimensions of flowers: 4 mm in diameter and 4 mm in height. Longevity on plant: Approximately 4 weeks. Longevity as cut flower: Not applicable. Persistent or self-cleaning: Persistent. Petals: Appearance: Dull. Texture: Smooth. Arrangement: Rotate. Number: An average of 4. Fused or unfused: Unfused. Shape: Ovate. Margin: Entire. Tip: Acute. Dimensions: An average of 2 mm in length and 1.2 mm in width. Color (adaxial): N79D with 83B margins. Color (abaxial): 77B. Color when faded: Does not fade. Petaloids: None. Sepals: Found only on flowers without bracts. Appearance: Smooth, dull. Arrangement: Rotate. Number: An average of 5. Shape: Ovate, lower 60% fused. Margin: Entire. Apex: Acute. Base: Cuneate. Dimensions: An average of 2.5 mm in length and 1 mm in width. Color (adaxial and abaxial): 144C. Calyx shape: Campanulate. Calyx dimensions: An average of 2.5 mm in length and 3 mm in diameter. Peduncle dimensions: An average 7.2 cm in length and 3 mm in diameter. Peduncle angle: Average angle is 30° where vertical is 0°. Peduncle color: 144A. Pedicel: Dimensions on flowers with bracts: An average of 2.1 cm in length and 1 mm in width. Dimensions on flowers without bracts: An average of 5 mm in length and 0.8 mm in width. Angle on flowers with bracts: 25° where vertical is 0°. Angle on flowers without bracts: 15° where vertical is 0°. Strength: Moderate. Color on flowers with bracts: 70B. Color on flowers without bracts: Between 147C and 147D. Bracts: Number per flower: 4. Shaped: Broad elliptic to obovate. Margins: Entire. Apex: Rounded. Base: Cuneate. Dimensions: An average of 2 cm in length and 1.4 cm in width. Color of immature adaxial surface: 75A with margins 76D or lighter. Color of immature abaxial surface: 75A with margins 76D or lighter. Color of mature adaxial surface: 75A with margins 76D or lighter. Color of mature abaxial surface: Between 75B and 77D with margins 76D or lighter.

Reproductive organs:

*Stamen number.*—An average of 10.

*Anther shape.*—Kidney-shaped.

*Anther length.*—An average of 0.8 mm.

*Anther color.*—Between N187B and 187C.

*Filament length.*—An average of 2 mm.

*Filament color.*—70B.

*Amount of pollen.*—Low.

*Pollen color.*—198D.

*Pistil number.*—An average of 3.

*Pistil length.*—An average of 1.3 mm.

*Stigma shape.*—Club-shaped.

*Stigma color.*—Between N187C and N187D.

*Style length.*—An average of 1 mm.

*Style color.*—N187D.

*Ovary color.*—144B.

Seed production: No seed production has been observed to date.

It is claimed:

1. A new and distinct cultivar of *Hydrangea* plant named 'RIE 13' as described and illustrated herein.

* * * * *